US011583169B2

(12) United States Patent
Huang et al.

(10) Patent No.: US 11,583,169 B2
(45) Date of Patent: Feb. 21, 2023

(54) OPTICAL FIBER SCANNING PROBE AND ENDOSCOPE HAVING THE SAME

(71) Applicant: INDUSTRIAL TECHNOLOGY RESEARCH INSTITUTE, Hsinchu (TW)

(72) Inventors: Chun-Chieh Huang, Hsinchu (TW); Yuan Chin Lee, Hsinchu (TW); Chi Shen Chang, Zhubei (TW); Hung Chih Chiang, Chiayi (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 326 days.

(21) Appl. No.: 16/987,744

(22) Filed: Aug. 7, 2020

(65) Prior Publication Data

US 2021/0186313 A1 Jun. 24, 2021

Related U.S. Application Data

(60) Provisional application No. 62/953,010, filed on Dec. 23, 2019.

(30) Foreign Application Priority Data

May 22, 2020 (TW) .................. 109117181

(51) Int. Cl.
  *A61B 1/00* (2006.01)
  *G02B 26/10* (2006.01)
  (Continued)

(52) U.S. Cl.
  CPC ...... *A61B 1/00172* (2013.01); *A61B 1/00032* (2013.01); *A61B 1/00165* (2013.01);
  (Continued)

(58) Field of Classification Search
CPC combination set(s) only.
See application file for complete search history.

(56) References Cited

U.S. PATENT DOCUMENTS 6,294,775 B1   9/2001   Seibel et al.
6,485,413 B1  11/2002   Boppart et al.
(Continued)

FOREIGN PATENT DOCUMENTS

CN   1586402 A   3/2005
CN   1933761 A   3/2007
(Continued)

OTHER PUBLICATIONS

Munce et al. "Electrostatic forward-viewing scanning probe for Doppler optical coherence tomography using a dissipative polymer catheter" Apr. 1, 2008.
(Continued)

*Primary Examiner* — Aaron B Fairchild
*Assistant Examiner* — Stephen Floyd London
(74) *Attorney, Agent, or Firm* — Maschoff Brennan

(57) ABSTRACT

An optical fiber scanning probe includes a rotor and at least one optical fiber. The rotor includes a torque rope rotatable about its central axis. The optical fiber is disposed on the rotor and eccentric relative to the torque rope. A central axis of the optical fiber is substantially parallel to the central axis of the torque rope. When the torque rope rotates about its central axis, the rotor brings a free end of the optical fiber to scan along an arc path.

9 Claims, 7 Drawing Sheets

(51) Int. Cl.
  *H04N 5/225* (2006.01)
  *A61B 5/00* (2006.01)
  *A61B 1/05* (2006.01)

(52) U.S. Cl.
  CPC ......... *G02B 26/103* (2013.01); *H04N 5/2252* (2013.01); *A61B 1/05* (2013.01); *A61B 5/0066* (2013.01); *A61B 5/0084* (2013.01); *H04N 2005/2255* (2013.01)

(56) References Cited

U.S. PATENT DOCUMENTS

| | | | |
|---|---|---|---|
| 6,975,898 B2 | 12/2005 | Seibel | |
| 7,338,439 B2 | 3/2008 | Kanai | |
| 7,566,300 B2 * | 7/2009 | Devierre | A61B 1/00128 600/106 |
| 7,616,986 B2 | 11/2009 | Seibel et al. | |
| 2005/0272976 A1 * | 12/2005 | Tanaka | A61B 1/0016 600/114 |
| 2007/0078305 A1 * | 4/2007 | Teramura | A61B 5/0066 600/139 |
| 2011/0098530 A1 * | 4/2011 | Yamane | A61B 1/00172 600/109 |
| 2013/0345510 A1 * | 12/2013 | Hadani | A61B 1/018 600/113 |
| 2014/0168654 A1 * | 6/2014 | Lin | A61B 5/0084 356/446 |
| 2015/0031948 A1 * | 1/2015 | Wood | A61B 1/00098 600/137 |
| 2015/0173622 A1 * | 6/2015 | Parto | A61B 18/20 600/478 |
| 2015/0359510 A1 * | 12/2015 | Currlin | A61B 8/0891 600/467 |
| 2016/0202417 A1 * | 7/2016 | Bhagavatula | A61B 5/0066 385/31 |
| 2016/0223754 A1 * | 8/2016 | Yamazaki | G03B 15/03 |
| 2017/0143196 A1 | 5/2017 | Liang et al. | |
| 2017/0280980 A1 * | 10/2017 | Yasunaga | A61B 1/00183 |
| 2019/0125377 A1 | 5/2019 | Shelton, IV | |

FOREIGN PATENT DOCUMENTS

| | | | |
|---|---|---|---|
| CN | 105658270 A | | 6/2016 |
| CN | 105848562 | | 8/2016 |
| CN | 106691373 | | 5/2017 |
| CN | 107529958 A | | 1/2018 |
| CN | 109497947 A | | 3/2019 |
| CN | 109799608 | | 5/2019 |
| KR | 20050072601 A | * | 7/2005 |
| TW | 394902 | | 6/2000 |
| TW | M309416 U | | 4/2007 |
| TW | I403301 | | 8/2013 |
| WO | 2016/167205 A1 | | 10/2016 |
| WO | 2019/133363 A1 | | 7/2019 |

OTHER PUBLICATIONS

Gora et al. "Endoscopic optical coherence tomography: technologies and clinical applications" May 1, 2017.
Michael Conry, et al. "Paired-angle-rotation scanning optical coherence tomography forward-imaging probe" May 1, 2006.
Wu et al. "Scanning all-fiber-optic endomicroscopy system for 3D nonlinear optical imaging of biological tissues" May 11, 2009.
Min et al. "Single-body lensed-fiber scanning probe actuated by magnetic force for optical imaging" Jun. 15, 2009.
Min et al. "Two-dimensional scanning probe driven by a solenoid-based single actuator for optical coherence tomography" Jun. 1, 2011.
Ryu et al. "Lensed fiber probes designed as an alternative to bulk probes in optical coherence tomography" Mar. 28, 2008.
Sun et el. "Review: Optical Scanning Probe for Optical Coherence Tomography" Oct. 2, 2013.
Chinese Office Action issued in corresponding application No. 202010528614.2, dated Mar. 22, 2022.
Taiwanese Office Action issued in corresponding application No. 109117181, dated Nov. 20, 2020.

* cited by examiner

OPTICAL FIBER SCANNING PROBE AND ENDOSCOPE HAVING THE SAME

CROSS-REFERENCE TO RELATED APPLICATIONS

This non-provisional application claims priority under 35 U.S.C. § 119(a) on Patent Application No. U.S. 62/953,010 filed in U.S. on Dec. 23, 2019, and Patent Application No(s). 109117181 filed in Taiwan R.O.C. on May 22, 2020, the entire contents of which are hereby incorporated by reference.

BACKGROUND

1. Technical Field

This present disclosure relates to an optical fiber scanning probe and an endoscope including the optical fiber scanning probe.

2. Related Art

Optical coherence tomography (OCT), which is a rapidly developing endovascular imaging technology in recent years, reconstructs two-dimensional or three-dimensional structure of biological tissues by optical scanning. OCT features non-free energy field source, high resolution, high speed scanning and imaging. At present, the most common application of OCT is a fiber scanning probe disposed on the distal end of the endoscope or cardiac catheter, and biological tissues from organisms can be examined by the fiber scanning probe. OCT is a clinically available technology to provide clear tissue image in vivo. With OCT, we could effectively find lesions to the organisms in vivo and select appropriate treatment, thereby improving medical quality and postoperative recovery.

As to a conventional OCT system, in order to implement two-dimensional CT imaging, a scanning mechanism should be provided at the sample arm. Usually, in order to achieve the scanning mechanism, electricity or electromagnetic force is applied on an optical fiber to drive the optical fiber to swing. This poses electric shock or electromagnetic interference to human tissues, which leads to medical risks during endoscopy or cardiac catheter treatments. In addition, as to the movement of fiber, the fiber can be driven by applying force at the bottom of the fiber, so the output end of the fiber actually has a change in inclination. This will require the adjustment of the optical path with the optical lens set, so the architecture is complicated and not conducive to miniaturize the fiber scanning probe.

SUMMARY

According to one embodiment of the present disclosure, an optical fiber scanning probe includes a rotor and at least one optical fiber. The rotor includes a torque rope rotatable about its central axis. The optical fiber is disposed on the rotor and eccentric relative to the torque rope. A central axis of the optical fiber is substantially parallel to the central axis of the torque rope. When the torque rope rotates about its central axis, the rotor brings a free end of the optical fiber to scan along an arc path.

According to another embodiment of the present disclosure, an endoscope includes a housing, an image sensor and the aforementioned optical fiber scanning probe. The image sensor and the optical fiber scanning probe are disposed in the housing, and an axial extending direction of the optical fiber scanning probe is substantially parallel to an axial extending direction of the image sensor.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

According to the present disclosure, the descriptions "element A is eccentric relative to element B" and "element A is eccentrically disposed on/in element B" are directed to that the center of element A is spaced apart from the center of element B. In some cases, it is more specifically directed to that the central axis of element A is spaced apart from the central axis of element B; that is, element A is not coaxial with element B.

Figure 1:
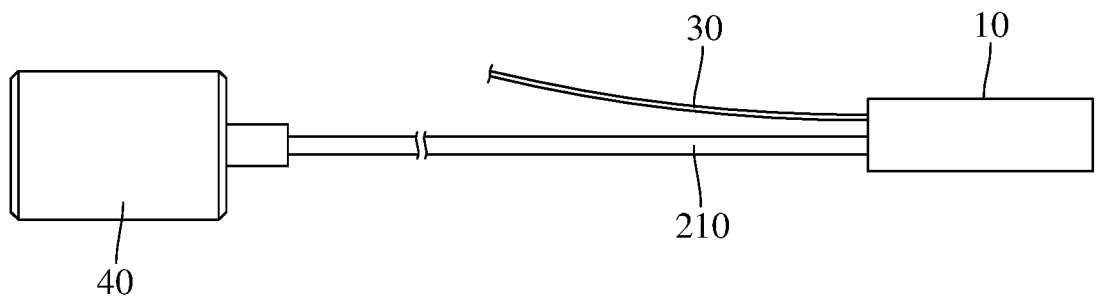
FIG. 1 is a schematic view of an optical fiber scanning probe according to a first embodiment of the present disclosure.
Figure 2:
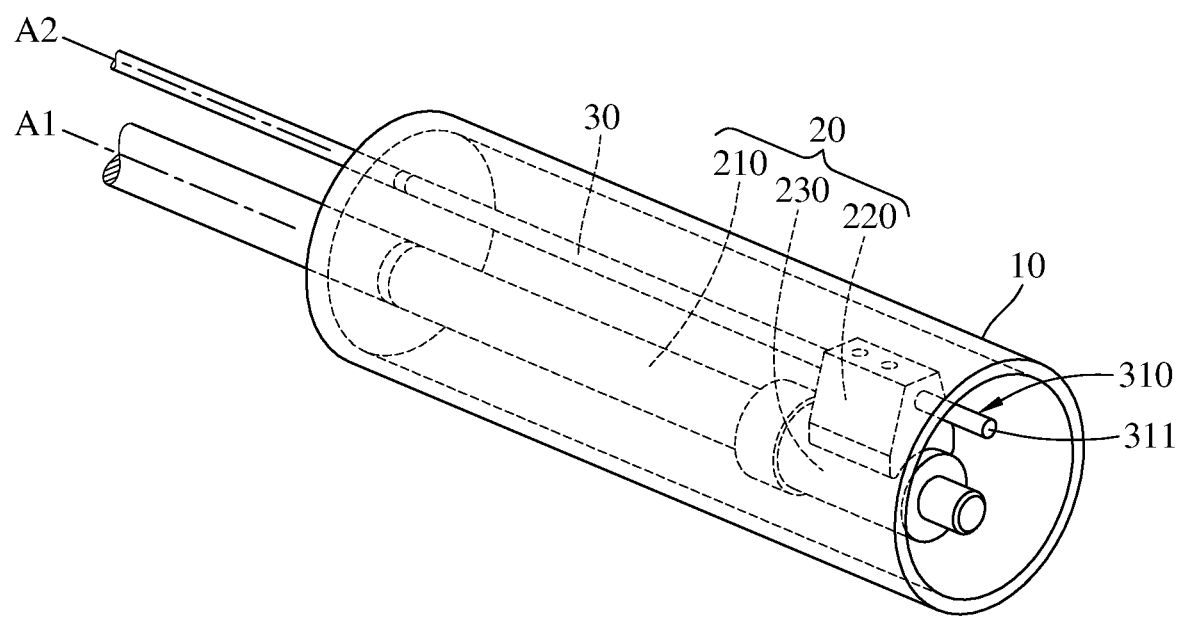
FIG. 2 is a perspective view of the optical fiber scanning probe in FIG. 1.

According to one embodiment of the disclosure, an optical fiber scanning probe includes a rotor and at least one optical fiber. Please refer to FIG. 1 and FIG. 2. FIG. 1 is a schematic view of an optical fiber scanning probe according to a first embodiment of the present disclosure, and FIG. 2 is a perspective view of the optical fiber scanning probe in FIG. 1. In this embodiment, an optical fiber scanning probe 1a includes a probe casing 10, a rotor 20, an optical fiber 30 and a power source 40. The rotor 20 and the optical fiber 30 are provided with their front portion disposed in the probe casing 10.

The rotor 20 includes a torque rope 210, a holder 220 and a sleeve 230. The torque rope 210 is rotatable about a central axis A1 of the torque rope 210. The front portion of the torque rope 210, the holder 220 and the sleeve 230 are disposed in the probe casing 10. In detail, the holder 220, for example but not limited to, is a protrusion. The sleeve 230 is sleeved outside the torque rope 210, and the holder 220 is disposed on the outer surface of the sleeve 230. When the torque rope 210 rotates relative to the probe casing 10, the torque rope 210 brings the holder 220 to rotate together.

Figure 3:
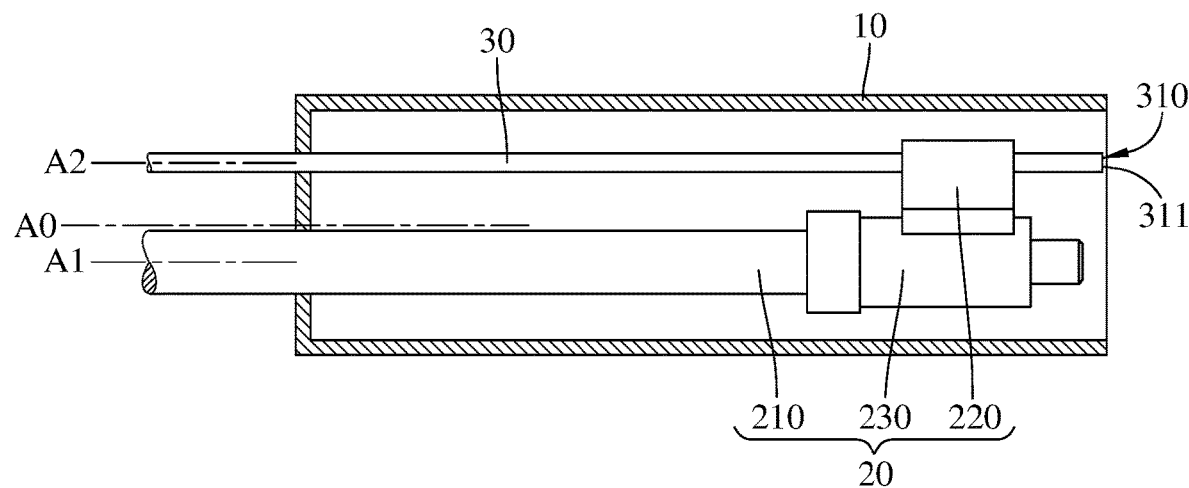
FIG. 3 is a side view showing interior of the optical fiber scanning probe in FIG. 2.
Figure 4:
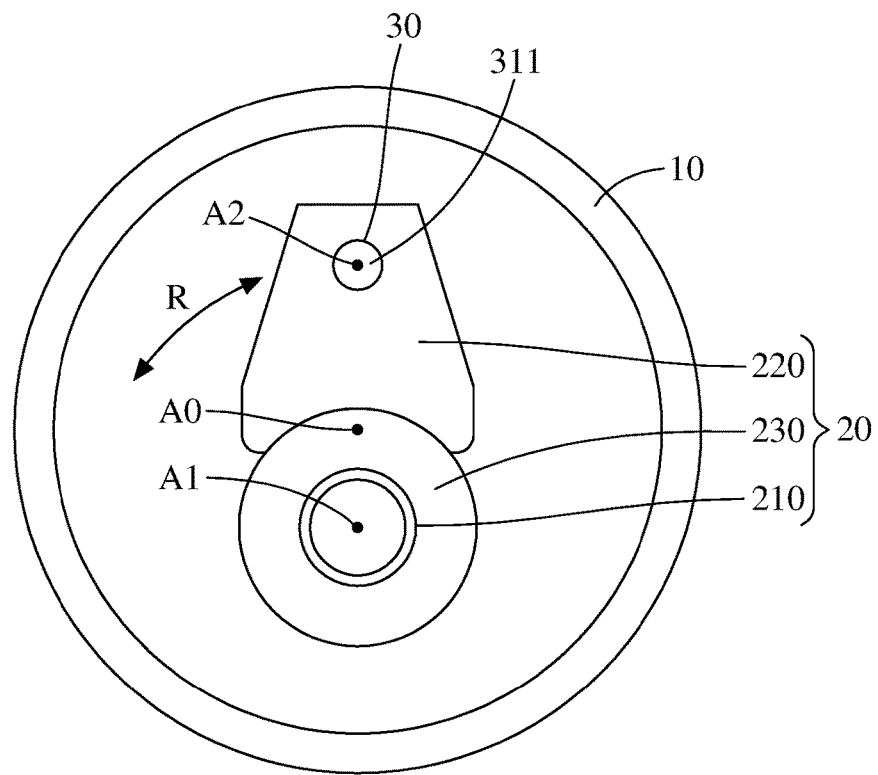
FIG. 4 is a front view showing interior of the optical fiber scanning probe in FIG. 2.

Please further refer to FIG. 3 and FIG. 4. FIG. 3 is a side view showing interior of the optical fiber scanning probe in FIG. 2, and FIG. 4 is a front view showing interior of the optical fiber scanning probe in FIG. 2. The optical fiber 30 is eccentric relative to the rotor 20; herein, this description means that the central axis A2 of the optical fiber 30 is spaced apart from the central axis A1 of the torque rope 210. The optical fiber 30 is disposed on the holder 220 of the rotor 20. The central axis A2 of the optical fiber 30 is spaced apart from and substantially parallel to the central axis A1 of the torque rope 210.

The power source 40 is, for example but not limited to, a servomotor disposed outside the probe casing 10, and the torque rope 210 of the rotor 20 is connected with the power source 40. The power source 40 drives the torque rope 210 to rotate relative to the probe casing 10.

When the torque rope 210 of the rotor 20 rotates about the central axis A1 of the torque rope 210, the rotor 20 brings a free end 310 of the optical fiber 30 to scan along an arc path R since the optical fiber 30 is disposed eccentrically. Every portion of the torque rope 210 does not generate torsional deformation during the rotation of the torque rope 210, and the optical fiber 30 is disposed on the holder 220 of the rotor 20, such that the movement of the free end 310 of the optical fiber 30 along the radial direction of the torque rope 210 can be prevented. The torque rope 210 is free of torsional deformation, and said free of torsional deformation (the torque rope 210 does not generate torsional deformation) includes a situation that no torsional deformation in the torque rope 210 and the other situation that the torque rope 210 generates small degree of torsional deformation, while this slight torsional deformation cannot affect the movement of the optical fiber 30.

There is an end facet 311 on the free end 310 of the optical fiber 30. When the rotor 20 rotates, the rotation of the torque rope 210 without torsional deformation keeps a normal line of the end facet 311 substantially parallel to the central axis A1 of the torque rope 210. The constant orientation of the end facet 311 is favorable for correcting optical path without additional optical lens when scanning tissue specimen, thereby meeting the requirement of compactness of the optical fiber scanning probe 1a. Moreover, the power source 40 in this embodiment is disposed outside the probe casing 10, such that it is unnecessary to provide space in the probe casing 10 for accommodating the power source 40, and thus it is favorable for minimizing the probe casing 10 to improve the compactness of the optical fiber scanning probe 1a.

In this embodiment, the rotor 20 is eccentrically disposed in the probe casing 10; more specifically, the central axis A1 of the torque rope 210 is spaced apart from the central axis A0 of the probe casing 10. Therefore, the probe casing 10 provides sufficient amount of internal space for movement of the optical fiber 30 so as to lengthen the arc path R (effective scanning stroke), which makes the optical fiber 30 capable of scanning tissue specimen having larger area.

Figure 5:
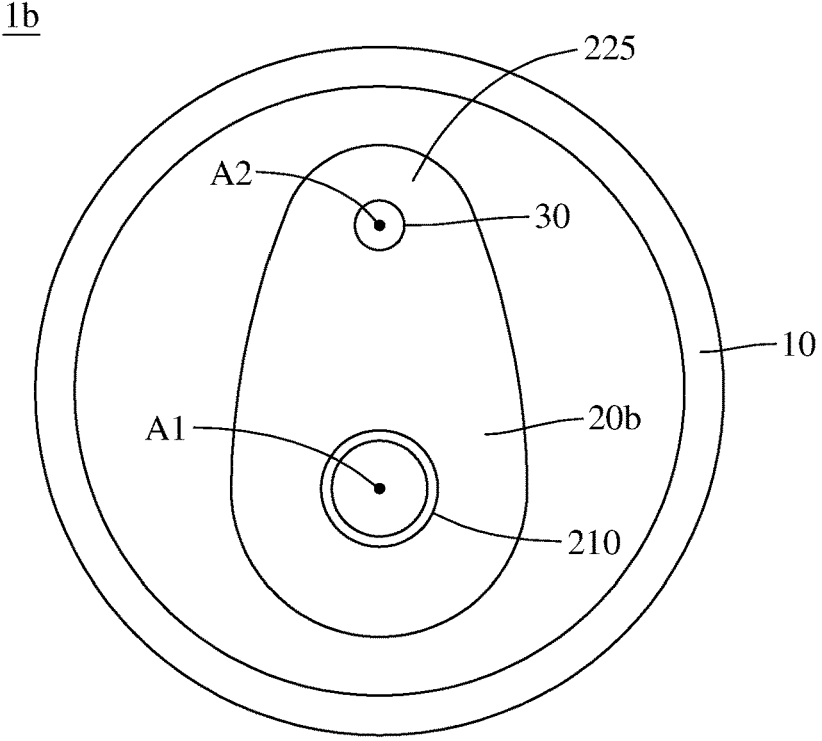
FIG. 5 is a front view showing interior of an optical fiber scanning probe according to a second embodiment of the present disclosure.

The rotor in the first embodiment includes torque rope, but the present disclosure is not limited thereto. Please refer to FIG. 5, which is a front view showing interior of an optical fiber scanning probe according to a second embodiment of the present disclosure. The second embodiment is similar to the first embodiment, and it is noted that an optical fiber scanning probe 1b in this embodiment includes a rotor 20b. The rotor 20b is disposed in the probe casing 10, and the rotor 20b includes a torque rope 210 and a rotating body 225. In detail, the rotating body 225 is a single piece including several parts which can be respectively interpreted as the holder 220 and the sleeve 230 of the rotor 20 in the first embodiment. The torque rope 210 and the optical fiber 30 are disposed on the rotating body 225, and the central axis A2 of the optical fiber 30 is spaced apart from (eccentric relative to) the central axis of the rotor 20b (that is, the central axis A1 of the torque rope 210). The rotating body 225 may be a disk which has any shape and is made of high stiffness material such as high carbon steel, stainless steel and polyamide. The distance between the central axis A2 of the optical fiber 30 and the central axis A1 of the torque rope 210 can be fixed so that the torsional deformation can be prevented during the rotation of torque rope 210.

Figure 6:
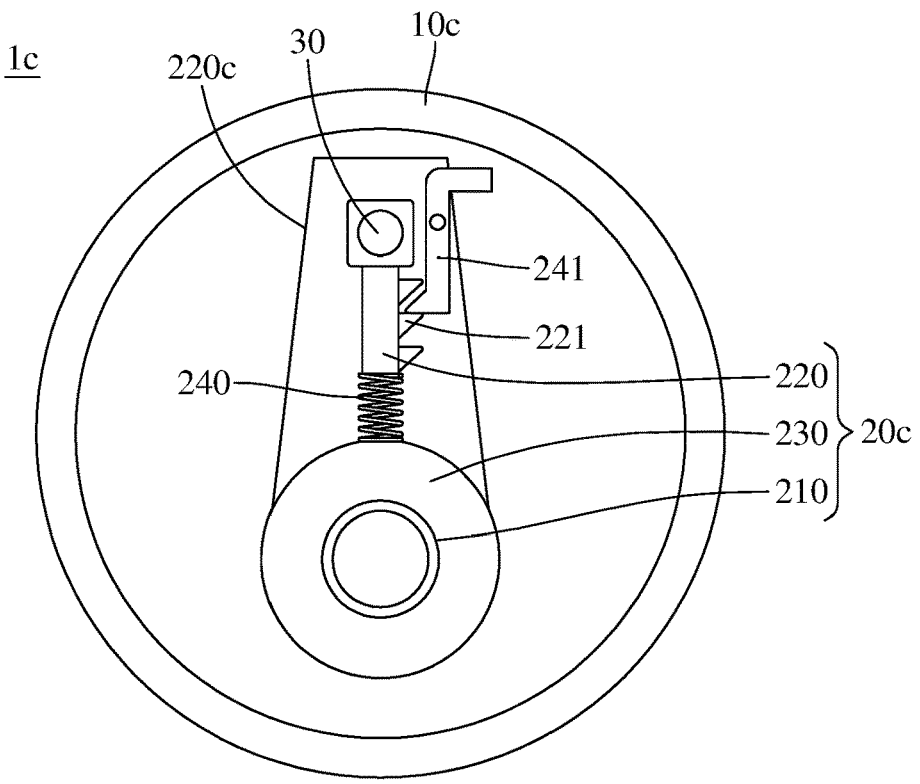
FIG. 6 is a front view showing interior of an optical fiber scanning probe according to a third embodiment of the present disclosure.

Please refer to FIG. 6, which is a front view showing interior of an optical fiber scanning probe according to a third embodiment of the present disclosure. The third embodiment is similar to the first embodiment, and it is noted that an optical fiber scanning probe 1c in this embodiment includes a probe casing 10c, a rotor 20c and an optical fiber 30. The rotor 20c includes a torque rope 210, a holder 220 and a sleeve 230 disposed in the probe casing 10c. The holder 220 is disposed on the outer surface of the sleeve 230 through an elastic member 240. The optical fiber scanning probe 1c further includes a base 220c disposed on the outer surface of the sleeve 230. The base 220c includes a pivotal component 241 rotatably disposed on the base 220c. The holder 220 includes a gear rack 221 which can be normally engaged with the pivotal component 241.

Figure 7:
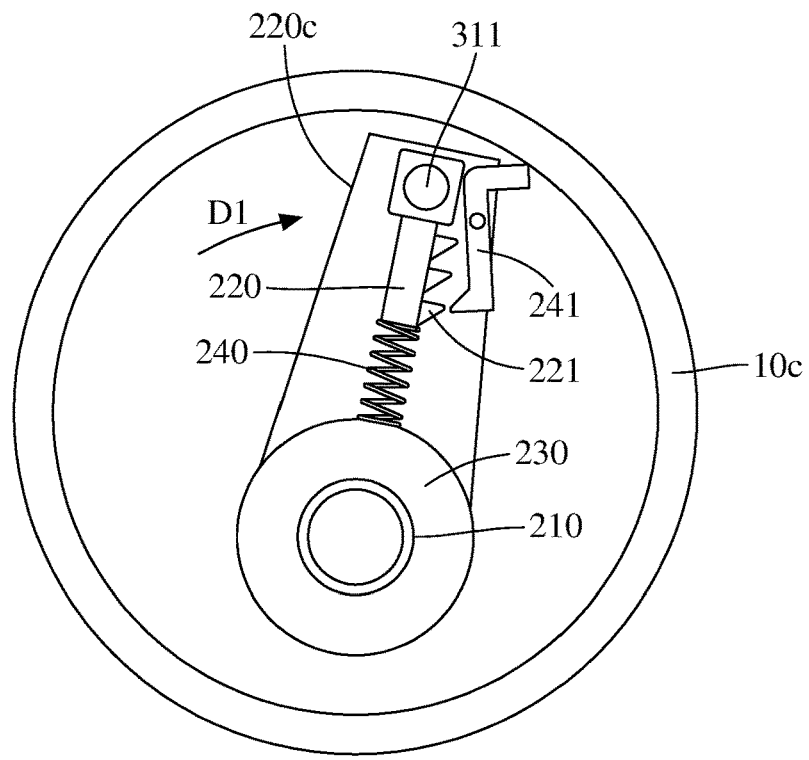
FIG. 7 and FIG. 8 are front views showing adjustment of the distance between the optical fiber and the torque rope in FIG. 6.

The gear rack 221 is separated from the pivotal component 241 or engaged with the pivotal component 241 by the interaction between the pivotal component 241 and the probe casing 10c, so as to adjust the distance between the central axis of the optical fiber 30 and the central axis of the torque rope 210. In detail, the pivotal component 241 works with the gear rack 221 to change the distance between two central axes of the optical fiber 30 and the torque rope 210 during the scanning of optical fiber 30. Please further refer to FIG. 7 and FIG. 8, which are front views showing adjustment of the distance between the optical fiber and the torque rope in FIG. 6. As shown in FIG. 7, the torque rope 210 rotates to bring the optical fiber 30 to scan along the first direction D1, and the rotation of torque rope 210 makes the pivotal component 241 contact the inner wall of the probe casing 10c. The pivotal component 241 is separated from the gear rack 221 due to the counter force from the probe casing 10c; at this time, since the pivotal component 241 is not engaged with the gear rack 221, the potential energy of elastic member 240 moves the holder 220 relative to the sleeve 230 so as to adjust the distance between the two central axes of the optical fiber 30 and the torque rope 210.

Figure 8:
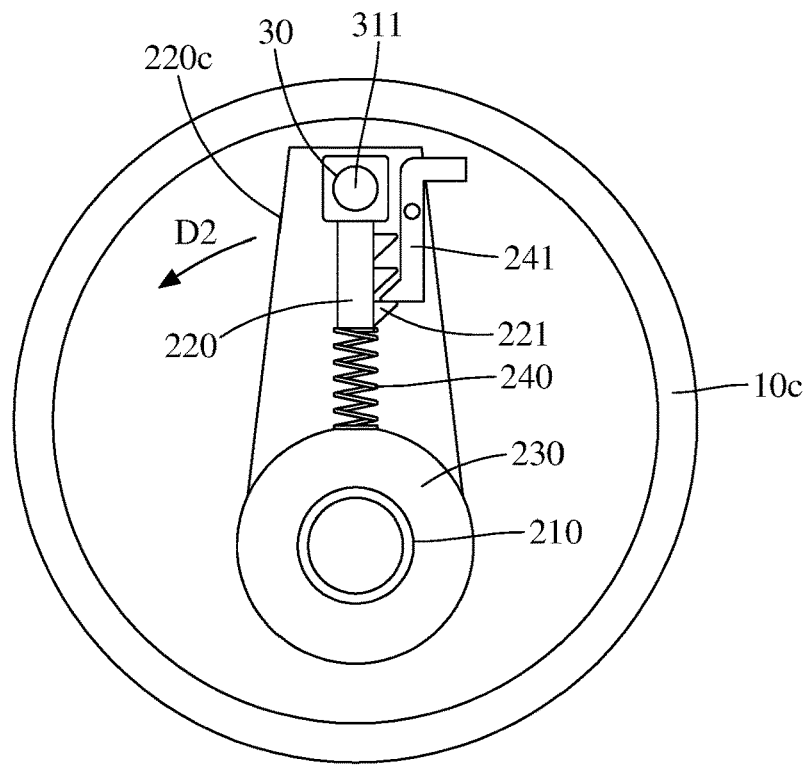

As shown in FIG. 8, the torque rope 210 rotates to bring the optical fiber 30 to scan along the second direction D2 opposite to the first direction D1, and the opposite movement of torque rope 210 makes the pivotal component 241 away from the inner wall of the probe casing 10c; at this time, the pivotal component 241 moves back to re-engaged with the gear rack 221. For example, after the pivotal component 241 moves away from the probe casing 10c, a torsional spring (not shown in the drawings) connected with the pivotal component 241 releases its potential energy to re-engage the pivotal component 241 with the gear rack 221. The engagement of the pivotal component 241 with the gear rack 221 can maintain the distance between the two central axes of the optical fiber 30 and the torque rope 210. Therefore, in a situation that the end facet 311 of the optical fiber 30 is maintained at a constant orientation, the optical fiber 30 can move along the radial direction of the torque rope 210 to change the distance between the two central axes of the optical fiber 30 and the torque rope 210, and thus the optical fiber scanning probe 1c is enabled to implement three-dimensional optical coherence tomography.

Figure 9:
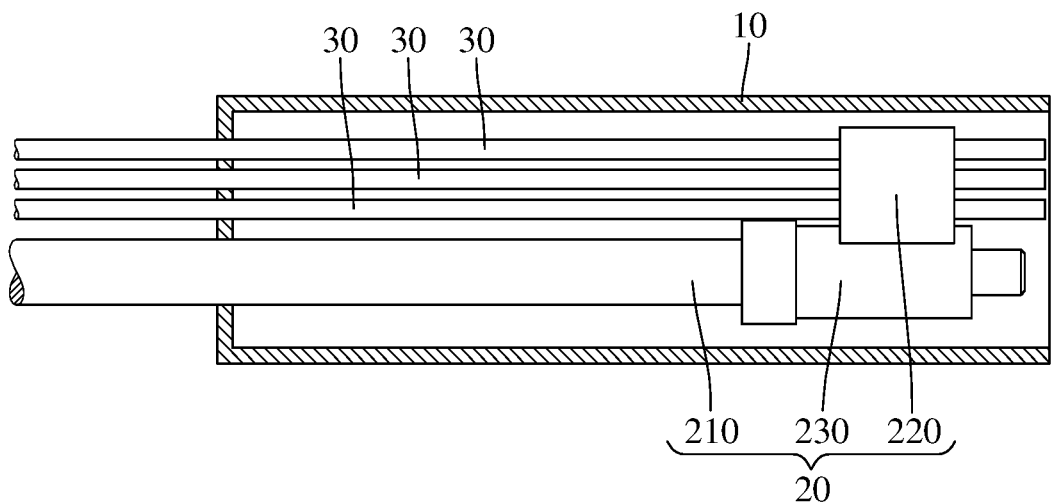
FIG. 9 is a side view showing interior of an optical fiber scanning probe according to a fourth embodiment of the present disclosure.
Figure 10:
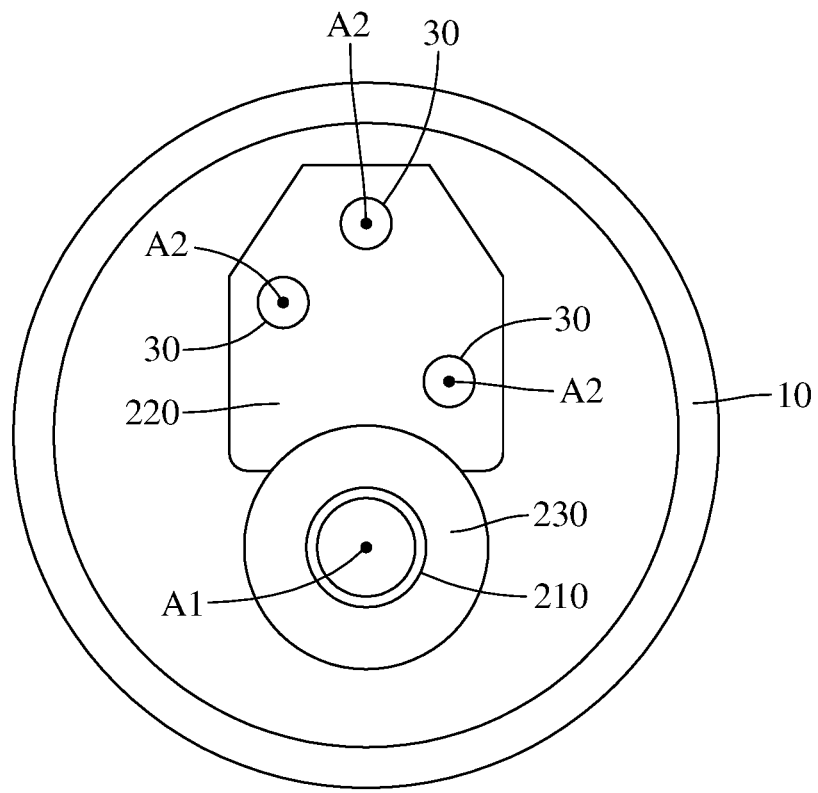
FIG. 10 is a front view showing interior of the optical fiber scanning probe in FIG. 9.

FIG. 9 is a side view showing interior of an optical fiber scanning probe according to a fourth embodiment of the present disclosure. FIG. 10 is a front view showing interior of the optical fiber scanning probe in FIG. 9. The fourth embodiment is similar to the first embodiment, and it is noted that an optical fiber scanning probe 1d in this embodiment includes a probe casing 10, a rotor 20 and multiple optical fibers 30. The optical fibers 30 are disposed on the holder 220 of the rotor 20, and the central axes A2 of the multiple optical fibers 30 are spaced apart from the central axis A1 of the torque rope 210 by a same distance or different distances. In one embodiment, it is more specific that the central axes A2 of the multiple optical fibers 30 are spaced apart from the central axis A1 by different radial distances. One optical fiber 30 close to the torque rope 210 and another optical fiber 30 far away from the torque rope 210 can scan different positions on the texture specimen for three-dimensional optical coherence tomography.

Figure 11:
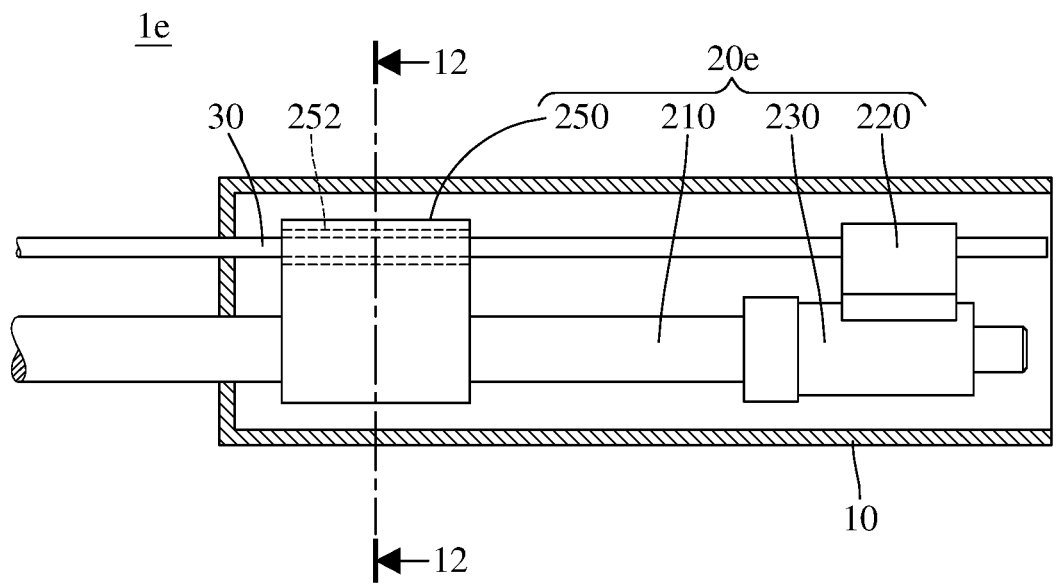
FIG. 11 is a side view showing interior of an optical fiber scanning probe according to a fifth embodiment of the present disclosure.
Figure 12:
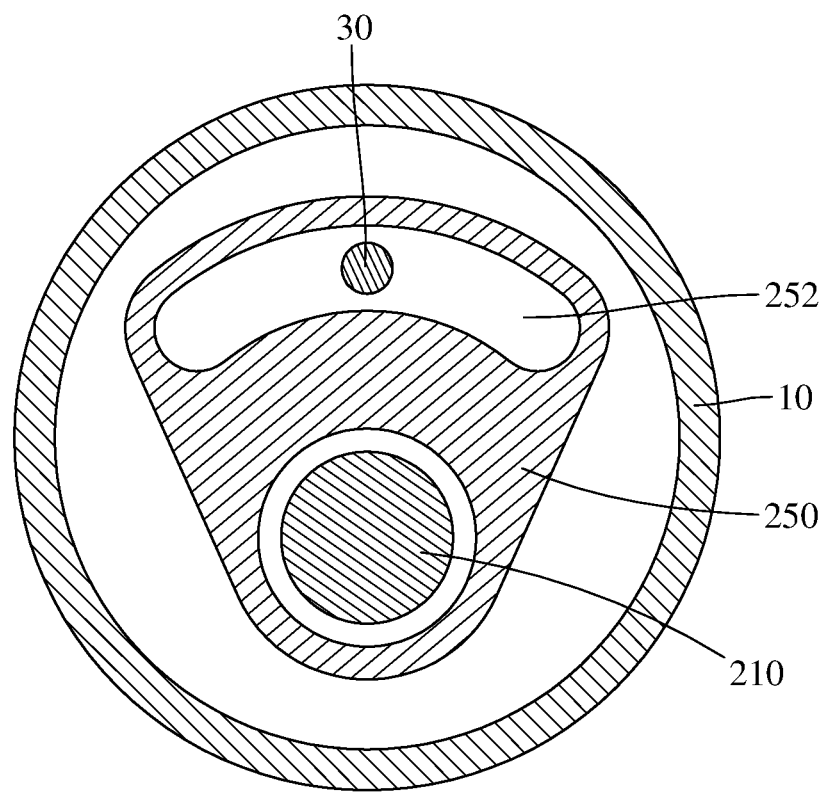
FIG. 12 is a cross-sectional view of the optical fiber scanning probe in FIG. 11 along line 12-12.

FIG. 11 is a side view showing interior of an optical fiber scanning probe according to a fifth embodiment of the present disclosure, and FIG. 12 is a cross-sectional view of the optical fiber scanning probe in FIG. 11 along line 12-12. The fifth embodiment is similar to the first embodiment, and it is noted that an optical fiber scanning probe 1e in this embodiment includes a rotor 20e, and the rotor 20e includes a torque rope 210, a holder 220, a sleeve 230 and an anchor 250. In detail, the sleeve 230 is sleeved outside the torque rope 210. The holder 220 is disposed on the outer surface of the sleeve 230, such that the holder 220 protrudes from the side surface of the torque rope 210. The torque rope 210 and the optical fiber 30 passes through the anchor 250, and the holder 220 is spaced apart from the anchor 250.

The anchor 250 has a through hole 252, and the optical fiber 30 passes through the through hole 252 of the anchor 250. In one embodiment, the size of the through hole 252 is larger than the diameter of optical fiber 30 in order to provide sufficient amount of space inside the through hole 252 for the movement and twist of the optical fiber 30. Thus, the rear portion of the optical fiber 30 is confined by the anchor 250. The anchor 250 can confine the scanning stroke of the optical fiber 30 so as to prevent the scanning optical fiber 30 from bending due to inertial force, thereby improving the stability of scanning optical fiber 30 and reducing the possibility of entanglement of the optical fiber 30 with the torque rope 210.

Figure 13:
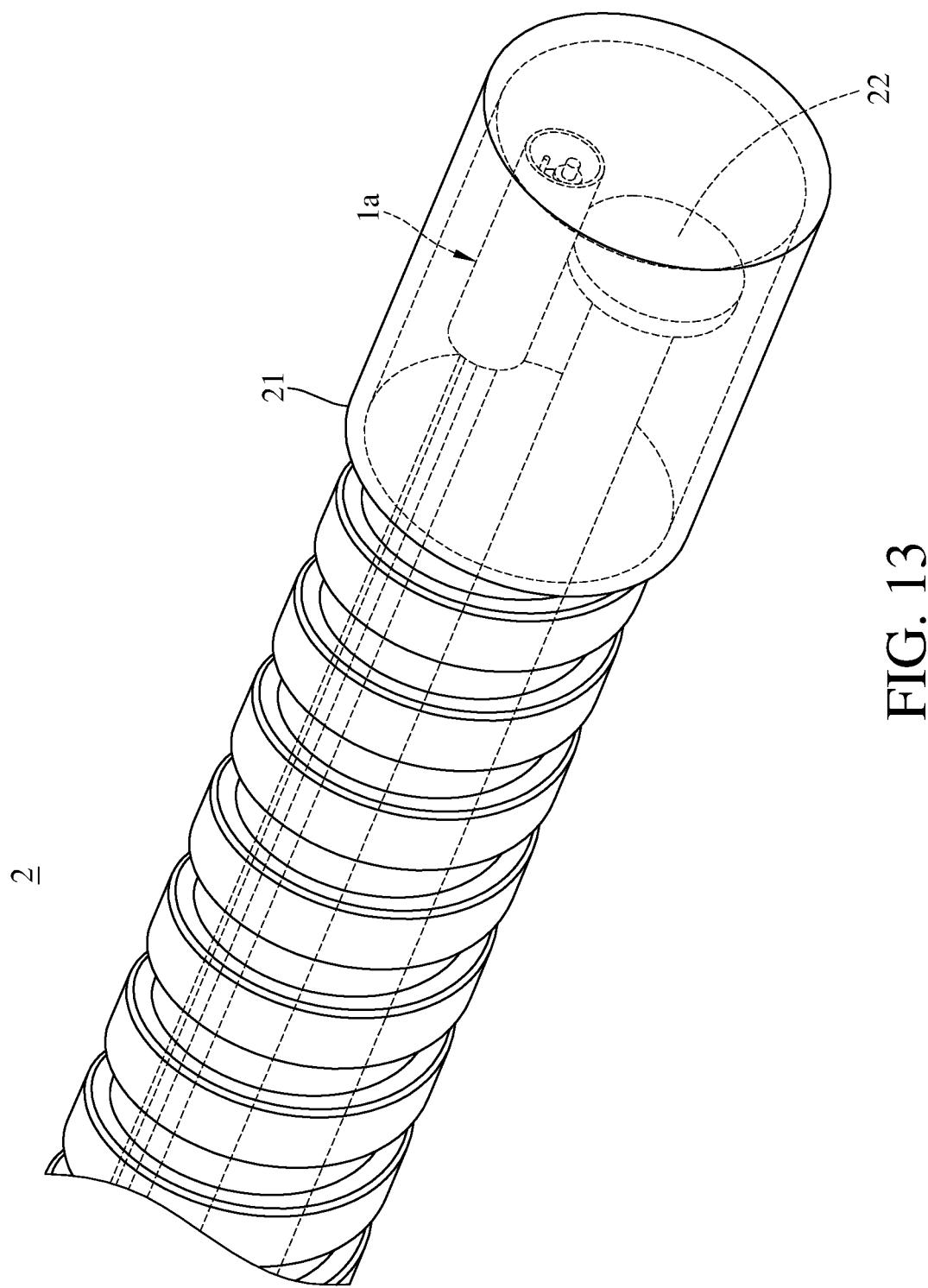
FIG. 13 is a schematic view of an endoscope according to one embodiment of the present disclosure.

The optical fiber scanning probe disclosed in the present disclosure is applicable to various kinds of optical device; for example, the optical fiber scanning probe may be taken as a scanning probe in an endoscope or a cardiac catheter. FIG. 13 is a schematic view of an endoscope according to one embodiment of the present disclosure. In this embodiment, an endoscope 2 includes a housing 21, an image sensor 22 and the optical fiber scanning probe in one of the aforementioned embodiments. FIG. 13 shows the endoscope 2 includes the optical fiber scanning probe 1a in the first embodiment and the image sensor 22. The optical fiber scanning probe 1a and the image sensor 22 are disposed in the housing 21. In detail, an axial extending direction of the optical fiber scanning probe 1a is substantially parallel to an axial extending direction of the image sensor 22. The housing 21 includes a bellow tube, such that the endoscope 2 can be bent to change the orientation of the optical fiber scanning probe 1a.

According to the present disclosure, when the torque rope rotates about its central axis, sine the optical fiber is eccentric relative to the torque rope, the rotor brings the free end of the optical fiber to scan along arc path. The orientation of the facet on the free end of the optical fiber is maintained during scanning, such that it is favorable for correcting optical path without additional optical lens when scanning tissue specimen, thereby meeting the requirement of compactness. Furthermore, the torque rope is free of torsional deformation during its rotation, such that the movement of the free end of the optical fiber along the radial direction of the torque rope can be prevented, and thus it is favorable for a stable image quality of optical coherence tomography.

Moreover, the power source for driving the rotor is disposed outside the probe casing, such that it is favorable for minimizing the probe casing to improve the compactness of the optical fiber scanning probe. As to the application to endoscope, the front portion of the optical fiber scanning probe may enter into organisms, and organisms can be protected from electric shock or electromagnetic interference since the power source is located outside the probe casing.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. An optical fiber scanning probe, comprising:
   a rotor comprising a torque rope, a holder and a sleeve, wherein the torque rope is rotatable about a central axis of the torque rope, the sleeve is sleeved outside the torque rope, the holder is disposed on an outer surface of the sleeve, and the holder is connected with the sleeve through an elastic member;
   at least one optical fiber disposed in the holder and eccentric relative to the torque rope, and a central axis of the at least one optical fiber being substantially parallel to the central axis of the torque rope;
   a probe casing, wherein the rotor and the at least one optical fiber are disposed in the probe casing;
   a base disposed on the outer surface of the sleeve; and
   a pivotal component rotatably disposed on the base;
   wherein when the torque rope rotates about the central axis of the torque rope, the rotor brings a free end of the at least one optical fiber to scan along an arc path;
   wherein the holder comprises a gear rack, the gear rack is separated from the pivotal component or engaged with the pivotal component by interaction between the pivotal component and the probe casing so as to adjust a distance between the central axis of the at least one optical fiber and the central axis of the torque rope.

2. The optical fiber scanning probe according to claim 1, wherein a line normal to an end facet of the free end of the at least one optical fiber is kept substantially parallel to the central axis of the torque rope when the torque rope rotates.

3. The optical fiber scanning probe according to claim 1, wherein a number of the at least one optical fiber is multiple, and central axes of the multiple optical fibers are spaced apart from the central axis of the torque rope by different distances.

4. The optical fiber scanning probe according to claim 1, wherein the rotor further comprises an anchor spaced apart from the holder, and the torque rope and the at least one optical fiber pass through the anchor.

5. The optical fiber scanning probe according to claim 4, wherein the anchor has a through hole, the at least one optical fiber passes through the through hole, and a size of the through hole is larger than a diameter of the at least one optical fiber.

6. The optical fiber scanning probe according to claim 1, further comprising a probe casing, wherein the rotor and the at least one optical fiber are disposed in the probe casing.

7. The optical fiber scanning probe according to claim 6, further comprising a power source disposed outside the probe casing, and the torque rope is connected with the power source.

8. The optical fiber scanning probe according to claim 1, wherein the rotor further comprising a rotating body, the torque rope and the at least one optical fiber are disposed on the rotating body, and the central axis of the at least one optical fiber is spaced apart from the central axis of the torque rope.

9. An endoscope, comprising:

a housing;

an image sensor; and the optical fiber scanning probe according to claim 1;

wherein the image sensor and the optical fiber scanning probe are disposed in the housing, and an axial extending direction of the optical fiber scanning probe is substantially parallel to an axial extending direction of the image sensor.

\* \* \* \* \*